(12) United States Patent
Lütticken et al.

(10) Patent No.: US 6,406,883 B1
(45) Date of Patent: Jun. 18, 2002

(54) **LMB GENE OF *STREPTOCOCCUS AGALACTIAE***

(76) Inventors: Rudolf Lütticken, Beulardsteiner Feld 25, D 52072 Aachen; Andreas Podbielski, Heilmeyersteige 158/4, D 89075, Ulm; Eva Rozdzinski, Gartenstr. 5, D 89077, Ulm; Barbara Spellerberg, Schlosswelherstr. 3-5, D 52077, Aachen, all of (DE)

( * ) Notice: Subject to any disclaimer, the term of this patent is extended or adjusted under 35 U.S.C. 154(b) by 0 days.

(21) Appl. No.: 09/160,975

(22) Filed: Sep. 25, 1998

Related U.S. Application Data

(60) Provisional application No. 60/059,952, filed on Sep. 26, 1997.

(51) Int. Cl.[7] ................................................ C12P 21/06

(52) U.S. Cl. ..................... 435/69.1; 536/23.7; 435/69.3; 435/320.1; 435/243; 435/252.3; 435/253.4; 424/244.1

(58) Field of Search ......................... 536/23.7; 435/69.1, 435/69.3, 320.1, 243, 252.3, 253.4; 424/244.1

(56) References Cited

PUBLICATIONS

Bentley et al. FEMS Immun. Med. Microbiol. 1995. 12(1):1–7 Abstract Only.*

* cited by examiner

*Primary Examiner*—Jennifer E. Graser
(74) *Attorney, Agent, or Firm*—Elliot M. Olstein; Raymond J. Lillie

(57) ABSTRACT

The present invention provides polynucleotides coding for the mature Lmb streptococcal adhesion mediator polypeptides. The polynucleotides were obtained from a genomic library obtained from Group B Streptococcus strain R268.

20 Claims, 12 Drawing Sheets

FIG. IA

```
TGATGTGATA AAAGATGGTA GTTTGTCATT GACAAAGCAT TGATAAGGAG TAAAATTAAC        60

TGGTTAATAA CTGGTTAAAT TATAATTGAG GAGGTACT ATG AAA AAA GTT TTT TTT      116
                                         Met Lys Lys Val Phe Phe
                                          -15

CTC ATG GCT ATG GTT GTG AGT TTA GTA ATG ATA GCA GGG TGT GAT            161
Leu Met Ala Met Val Val Ser Leu Val Met Ile Ala Gly Cys Asp
-10                  -5                                  5

AAG TCA GCA AAC CCC AAA CAG CCT ACG CAA GGC ATG TCA GTT GTA            206
Lys Ser Ala Asn Pro Lys Gln Pro Thr Gln Gly Met Ser Val Val
             10                   15                      20

ACC AGC TTT TAC CCA ATG TAT GCG ATG ACA AAA GAA GTA TCT GGA            251
Thr Ser Phe Tyr Pro Met Tyr Ala Met Thr Lys Glu Val Ser Gly
                 25                   30                      35

GAC GTA AAT GAT GTG AGG ATG ATC CAA TCA GGT GCG GGC ATT CAT            296
Asp Val Asn Asp Val Arg Met Ile Gln Ser Gly Ala Gly Ile His
                     40                   45                      50

TCC TTT GAA CCG TCT GTA AAT GAT GTG GCA GCT ATT TAT GAC GCG            341
Ser Phe Glu Pro Ser Val Asn Asp Val Ala Ala Ile Tyr Asp Ala
                         55                   60                      65
```

FIG. 1B

```
GAT TTG TTT GTT TAC CAT TCA CAT ACC TTA GAA GCT TGG GCA AGG     386
Asp Leu Phe Val Tyr His Ser His Thr Leu Glu Ala Trp Ala Arg
                 70                  75                  80

GAT CTA GAC CCT AAT TTA AAA AAA TCA AAG GTT AAC GTG TTT GAA     431
Asp Leu Asp Pro Asn Leu Lys Lys Ser Lys Val Asn Val Phe Glu
                 85                  90                  95

GCG TCA AAA CCT CTG ACA CTA GAT AGA GTC AAA GGG CTA GAA GAT     476
Ala Ser Lys Pro Leu Thr Leu Asp Arg Val Lys Gly Leu Glu Asp
                100                 105                 110

ATG GAA GTC ACA CAA GGC ATT GAC CCT GCG ACA CTT TAT GAC CCA     521
Met Glu Val Thr Gln Gly Ile Asp Pro Ala Thr Leu Tyr Asp Pro
                115                 120                 125

CAT ACC TGG ACG GAT CCC GTT TTA GCT GGT GAG GAA GCT GTT AAT     566
His Thr Trp Thr Asp Pro Val Leu Ala Gly Glu Glu Ala Val Asn
                130                 135                 140

ATC GCT AAA GAG CTA GGA CAT TTG GAT CCT AAA CAC AAA GAC AGT     611
Ile Ala Lys Glu Leu Gly His Leu Asp Pro Lys His Lys Asp Ser
                145                 150                 155
```

FIG. 1C

```
TAC ACT AAA AAG GCT AAG GCT TTC AAA AAA GAA GCA GAG CAA CTA      656
Tyr Thr Lys Lys Ala Lys Ala Phe Lys Lys Glu Ala Glu Gln Leu
            160                 165                 170

ACT GAA GAA TAC ACT CAA AAA TTT AAA AAG GTG CGC TCA AAA ACA      701
Thr Glu Glu Tyr Thr Gln Lys Phe Lys Lys Val Arg Ser Lys Thr
            175                 180                 185

TTT GTG ACG CAA CAC ACG GCA TTT TCT TAT CTG GCT AAA CGA TTC      747
Phe Val Thr Gln His Thr Ala Phe Ser Tyr Leu Ala Lys Arg Phe
            190                 195                 200

GGC TTG AAA CAA CTT GGT ATC TCG GGT ATT TCT CCA GAG CAA GAG      791
Gly Leu Lys Gln Leu Gly Ile Ser Gly Ile Ser Pro Glu Gln Glu
            205                 210                 215

CCC TCT CCT CGC CAA TTG AAA GAA ATT CAA GAC TTT GTT AAA GAA      836
Pro Ser Pro Arg Gln Leu Lys Glu Ile Gln Asp Phe Val Lys Glu
            220                 225                 230
```

FIG. 1D

```
TAC AAC GTC AAG ACT ATT TTT GCA GAA GAC AAC GTC AAC CCC AAA    881
Tyr Asn Val Lys Thr Ile Phe Ala Glu Asp Asn Val Asn Pro Lys
235             240             245

ATT GCT CAT GCT ATT GCG AAA TCA ACA GGA GCT AAA GTA AAG ACA    926
Ile Ala His Ala Ile Ala Lys Ser Thr Gly Ala Lys Val Lys Thr
250             255             260

TTA AGT CCA CTT GAA GCT GCT CCA AGC GGA AAC AAG ACA TAT CTA    971
Leu Ser Pro Leu Glu Ala Ala Pro Ser Gly Asn Lys Thr Tyr Leu
265             270             275

GAA AAT CTT AGA GCA AAT TTG GAA GTG CTC TAT CAA CAG TTG AAG   1026
Glu Asn Leu Arg Ala Asn Leu Glu Val Leu Tyr Gln Gln Leu Lys
280             285

TAA                                                            1029
```

FIG. 4
Ia Ib Ic
0.5 kb>
II IV III
0.5 kb>
      VII    V
VI    VIII
0.5 kb>
FIG. 5
1 2 3 4
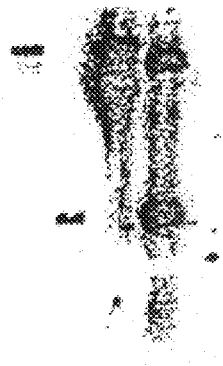

FIG. 8

US 6,406,883 B1

LMB GENE OF STREPTOCOCCUS AGALACTIAE

This application claims priority under 35 U.S.C. 119(e) to U.S. Provisional Application No. 60/059,952, filed Sep. 26, 1997.

This invention relates to newly identified polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been putatively identified as Lmb streptococcal adhesion mediator that promotes attachment of *Streptococcus agalactiae* cells to human laminin.

Laminin is a 900 kDa glycoprotein that is a major component of the basement membrane. It is composed of three distinct polypeptide chains (A, B1, B2) which reversibly assemble to form the macromolecular structure. Functions of laminin include the formation of the basement membrane by interaction with other basement membrane components and the development and maintenance of cellular organization.

*S. agalactiae* has been demonstrated to damage the pulmonary epithelium (Nizei, Gibson et al. 1996) which leads to the exposure of underlying basement membrane structures. Adhesion to basement membrane components may be important for persistent bacterial colonization of damaged epithelium and invasion of bacteria into the bloodstream.

The adherence of bacteria to laminin may be important for the development of invasive group B streptococcal infection. Invasion of *S. agalactiae* into the blood stream as well as the entry into CSF, which occurs in the case of meningitis, requires the passage of bacteria through basement membranes. The interaction of bacterial surface proteins with laminin could be an important mechanism in this context. For *H. influenzae* adhesion and penetration of the basement membranes, which are open to circulation in the fenestrated endothelium of the choroid plexus, is discussed as the route of entry into the CSF (Virkola, Lähteenmäki et al. 1996).

Adhesion mediators of the LraI adhesion family mediate attachment of the streptococci pathogens to human laminin and contribute to streptococcal disease in humans. In particular, expression of cell surface receptors determines streptococcal adhesion properties which include binding to extracellular matrix proteins, epithelial cells, endothelial cells and to other bacterial organisms. The LraI (lipoprotein receptor antigen I) family of surface-associated lipoproteins is involved in co-aggregation of *Streptococcus gordonii* with *Actinomyces naeslundii*, the adherence of *S. sanguis* to the salivary pellicle, the binding of *S. parasanguis* to a platelet fibrin matrix (Viscount, Munro et al. 1997) (Jenkinson 1994) and the adherence of *S. pneumoniae* to type II pneumocytes (Berry and Paton 1996). Previously identified members of this family are PsaA from *Streptococcus pneumoniae*, FimA from *S. parasanguis*, SsaB from *S. sanguis*, EfaA from *Enterococcus faecalis* and ScbA from *S. crista* and ScaA from *S. gordonii*.

Genes of this family are located in ABC transporter type operons and thought to function as solute binding components in analogy to outer membrane proteins of gram-negative organisms (Jenkinson 1994) (Kolenbrander, Andersen et al. 1994). PsaA of *S. pneumoniae* and FimA of *S. parasanguis* have been shown to be essential for virulence in animal models (Viscount, Munro et al. 1997) (Berry and Paton 1996). In addition immunogenic properties were demonstrated for EfaA, FimA and PsaA indicating a potential use of these proteins as vaccine candidates.

*Streptococcus agalactiae* (Group B streptococcus, GBS) is one of the most important neonatal pathogen causing septicemia or meningitis in up to 1.8 cases per 1000 live births. Even with antibiotic therapy mortality rates range between 5 and 30% (Weisman, Stoll et al. 1992). In addition recent studies report an increasing number of serious infections in adults (Farley 1995) (Farley, Harvey et al. 1993). Several virulence factors that contribute to the pathogenesis of the disease have been identified. These include the capsule (Viessels, Rubens et al. 1989), the CAMP factor (Fehrenbach, Jürgens et al. 1988) (Podbielski, Blankenstein et al. 1994), the hemolysin (Nizet, Gibson et al. 1996) and C-protein on the bacterial surface (Michel, Madoffet al. 1991).

The adherence of *S. agalactiae* to immobilized fibronectin has also been implicated in the pathogenesis of disease (Tamura and Rubens 1995). However, prior to the present invention, genetic determinants for the adherence of *S. agalactiae* to extracellular matrix proteins had not been identified.

In accordance with one aspect of the present invention, there are provided novel Lmb streptococcal adhesion mediator polypeptides, as well as active fragments, analogs and derivatives thereof.

In accordance with another aspect of the present invention, there are provided isolated nucleic acid molecules encoding the Lmb streptococcal adhesion mediator polypeptides of the present invention including mRNAs, cDNAs, genomic DNAs as well as active analogs and fragments of such Lmb streptococcal adhesion mediator polypeptides.

In accordance with another aspect of the present invention there are provided isolated nucleic acid molecules encoding mature lmb polypeptides expressed by the DNA contained in ATCC strain Deposit No. 12400 utilizing the primes equences and procedures as described below, which maybe obtained by PCR, as construct of the article acid provided and a plasmid provided therefrom.

In accordance with yet a further aspect of the present invention, there is provided a process for producing such polypeptides by recombinant techniques comprising culturing recombinant prokaryotic and/or eukaryotic host cells, containing a nucleic acid sequence of the present invention, under conditions promoting expression of said Lmb streptococcal adhesion mediator polypeptides and subsequent recovery of said Lmb streptococcal adhesion mediator polypeptides.

In accordance with yet a further aspect of the present invention, there is provided a process for utilizing such Lmb streptococcal adhesion mediator polypeptides as reagents for testing pharmaceutical antibiotics for their activity in deactivating or controlling the activity of the Lmb streptococcal adhesion mediator polypeptides as part of a screening process to identify pharmaceuticals for treating or controlling streptococcal infections.

In accordance with another aspect of the present invention the polynucleotides or epitopic fragments thereof are useful as in vitro agents for producing monoclonal antibodies useful in screening procedures for diagnosing streptococcus bacterial infections by identifying the presence of such bacteria in a specimen from a mammal suspected of having such an infection. Also, such polynucleotides or epitopic fragments are useful as reagents to test pharmaceutical chemicals for activity in suppressing the expression of such polynucleotides. Thus, the polynucleotides and polypeptides according to the invention are useful as in vitro agents for diagnostic and screening procedures for identifying and/or treating streptococcal infections in mammals.

In another aspect of the present invention, an antisense construct prepared through the use of antisense technology, may be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., Nucl. Acids Res., 6:3073 (1979); Cooney et al, Science, 241:456 (1988); and Dervan et al., Science, 251: 1360 (1991)), thereby preventing transcription and the production of the streptococcal Imb genes. The antisense RNA oligonucleotide hybridizes to the MRNA in vivo and blocks translation of mRNA molecules into Lmb streptococcal adhesion mediator polypeptides (antisense -Okano, J. Neurochem., 56:560 (1991); Oligodeoxynucleotides as Antisense Inhibitors of Gene Expression, CRC Press, Boca Raton, FL (1988)). The oligonucleotides described above can also be delivered to cells such that the antisense RNA or DNA may be expressed in vivo to inhibit production of the Lmb streptococcal adhesion mediator polypeptides.

In accordance with yet a further aspect of the present invention, there are also provided nucleic acid probes comprising nucleic acid molecules of sufficient length to specifically hybridize to a nucleic acid sequence of the present invention.

In accordance with yet a further aspect of the present invention, there is provided a process for utilizing such Lmb streptococcal adhesion mediator polypeptides, or polynucleotides encoding such polynucleotides, for in vitro purposes related to scientific research, for example, to generate probes for identifying similar sequences which might encode similar Lmb streptococcal adhesion mediator polypeptides from other organisms by using certain regions, i.e., conserved sequence regions, of the nucleotide sequence.

In accordance with a still further aspect of the present invention, there are also provided vaccines which will cause a host to generate antibodies against the lmb polypeptide(s) according to the present invention. Such vaccines are useful in the treatment of hosts to avoid streptococcal infections or to diminish the severity of such infections. Further, pharmaceutical compositions that are useful as vaccines have an effective amount of at least one of the Imb polypeptide(s) according to the present invention are provided.

These and other aspects of the present invention should be apparent to those skilled in the art from the teachings herein.

BRIEF DESCRIPTION OF THE DRAWINGS

The following drawings are illustrative of an embodiment of the invention and are not meant to limit the scope of the invention as encompassed by the claims.

FIGS. 1A–1D, is a contiguous illustration of the full-length DNA sequence (SEQ ID NO: 1) and the corresponding deduced amino acid sequences for the Lmb streptococcal adhesion mediator polypeptide of the present invention, as well as another open reading frame and an intergenic region.

Figure 2A:
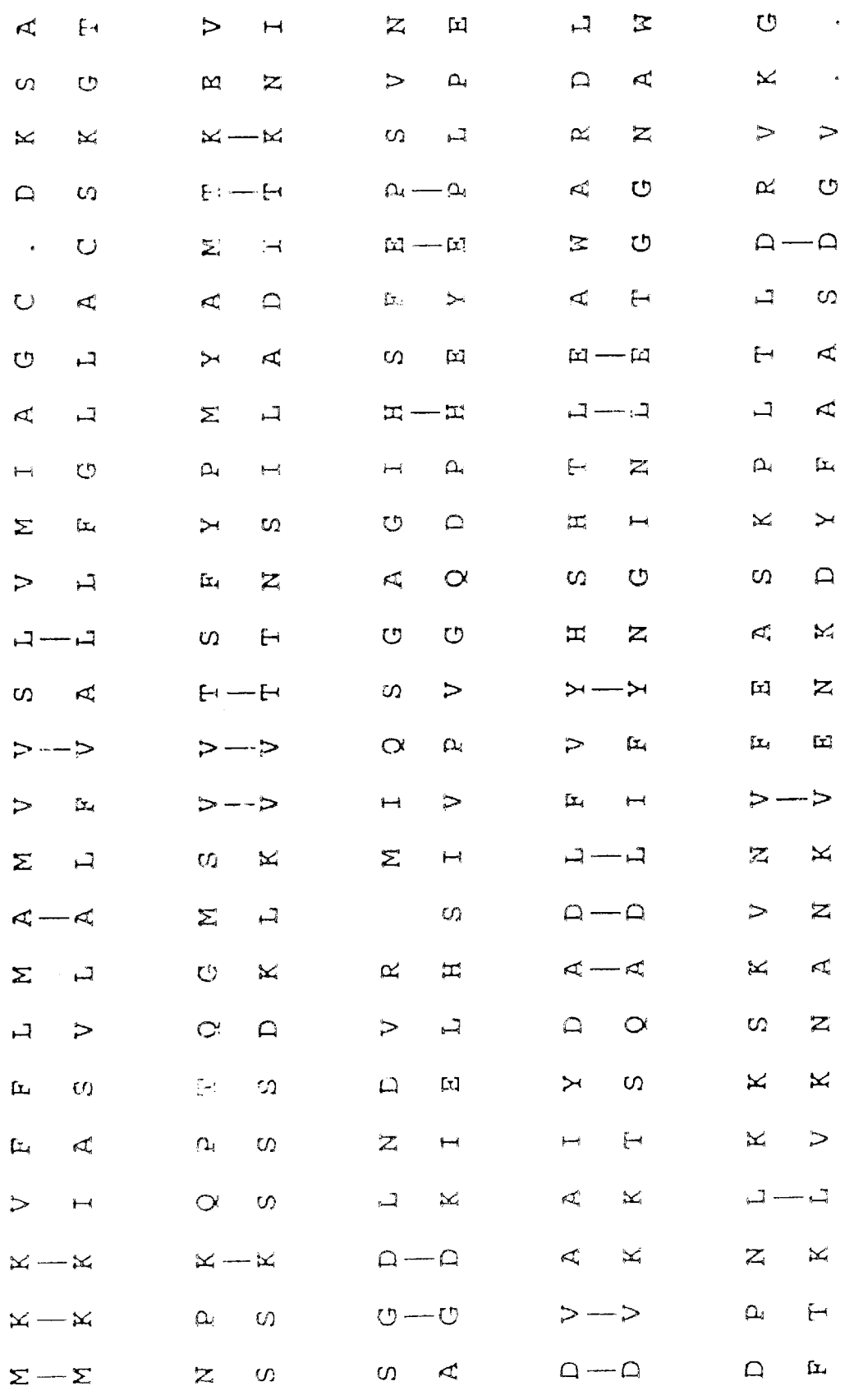
Figure 2C:
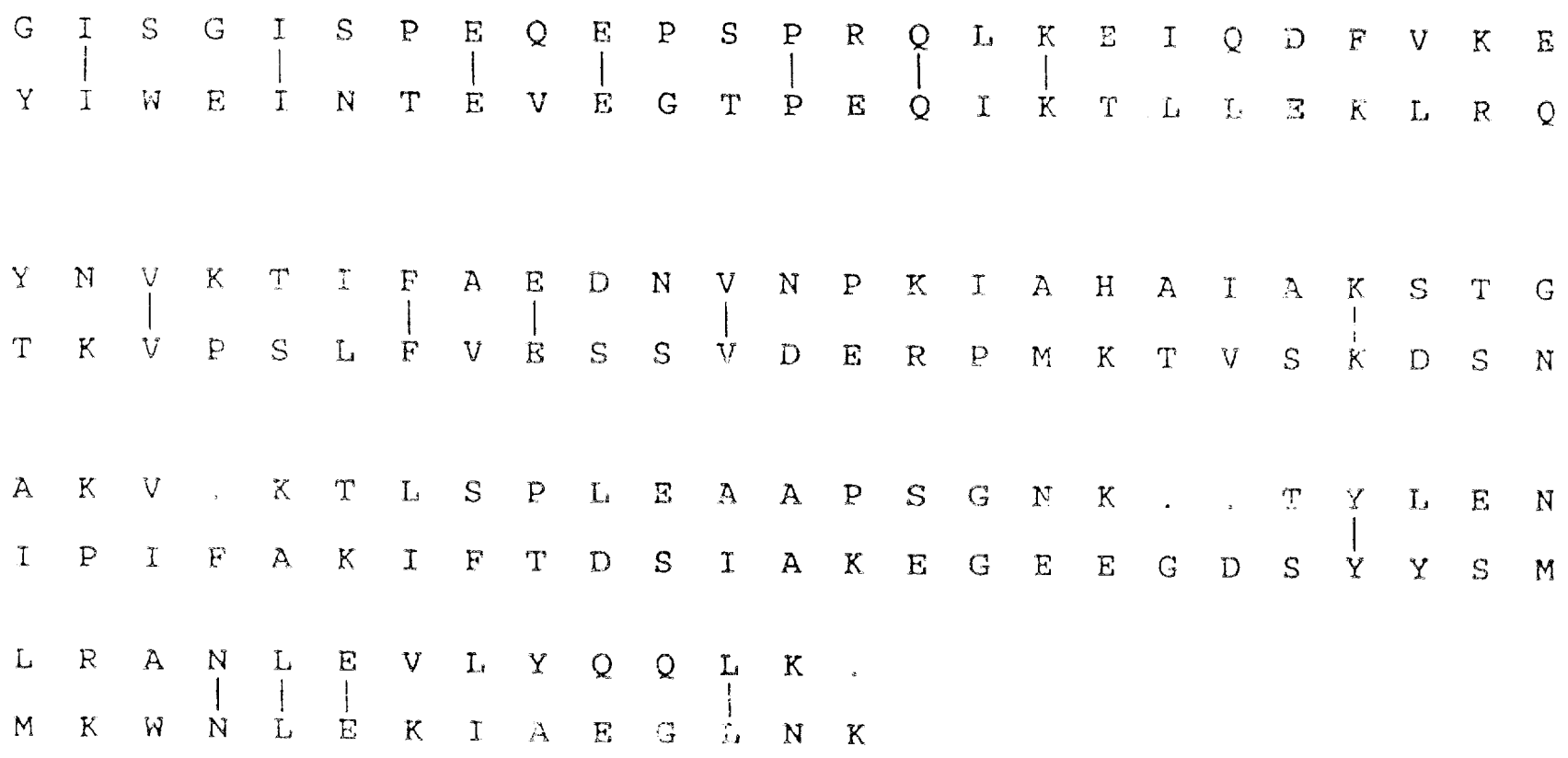

FIGS. 2A–2C is an example of the present lmb polypeptide sequence (SEQ ID NO:2) as compared to the psa polypeptide of S. pneumoniae.

FIG. 4 illustrates the comparison of the lmb gene in different group B streptococcal serotypes. A 430 bp fragment of lmb was amplified from genomic DNA by PCR. PCR products were transferred to a nylon membrane and detected by a Dig-dUTP labeled internal probe. Serotypes are indicated above each lane.

FIG. 5 illustrates the confirmation of a genomic plasmid insertion site in mutant lmb-k1. Chromosomal DNA of wildtype 090R and mutant lmb-k1 was digested with restriction enzymes XbaI or EcoRI, transferred to a nylon membrane and hybridized with a Dig dUTP labeled PCR product directed to the duplicated fragment of lmb. 090R/EcoRI (lane 1), 090R/XbaI (lane 2), lmb-k1 /EcoRI (lane 3), lmb-k1 /XbaI (lane 4).

FIG. 8 shows a comparison of the physical maps of the Lmb and the LraI domains. In the physical map of the lmb locus the lmb gene is designated by the open box showing a putative cleavage site for the signal peptidase II. A region corresponding to the $\alpha$ region of LraI proteins and demonstrating homology to the B2 chain of human laminin is indicated. Structural features of the LraI family are shown as proposed by Jenkinson. Numbers refer to amino acid residues, demarking four regions: Leader peptide, cleaved off by signal peptidase II, B1, B2 and the $\alpha$ region, which is presumed to be the solute binding domain.

DEFINITIONS

Figure 3:
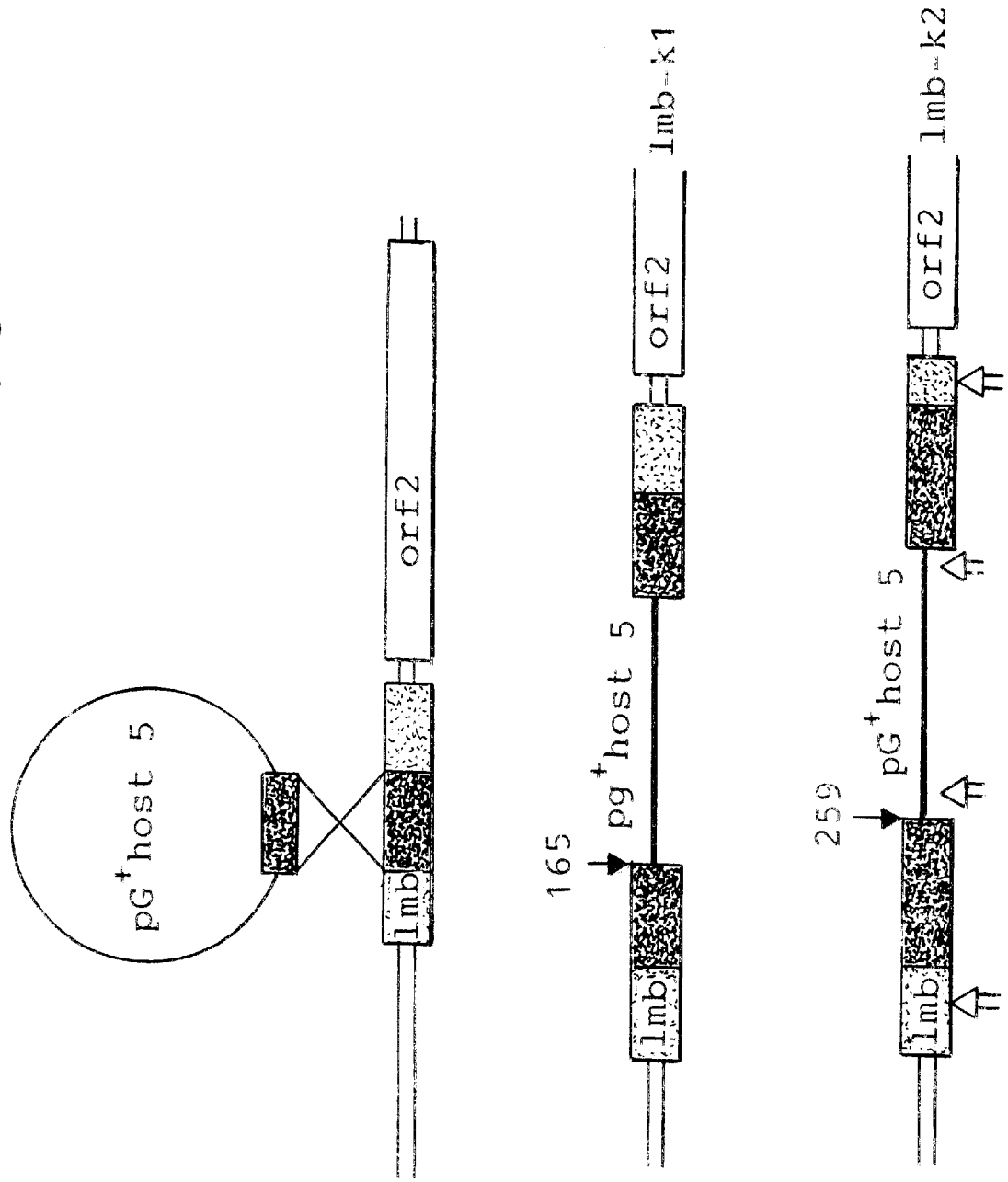
FIG. 3 illustrates the construct of Imb mutants by insertion of the plasmid pG+host 5 into the chromosome of GBS strain 090R. The amino acid residue at which a fusion to vector sequence occurs in mutant lmb-k1 and lmb0k1 is indicated in the FIG. 3 above the respective construct by arrows. Primer binding sites that were used to confirm correct integration of the plasmid in mutant lmb-k2 are shown as open arrows.

In order to facilitate understanding of the following description and examples which follow certain frequently occurring methods and/or terms will be described.

The term "gene" means the segment of DNA involved in producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single MRNA, which is then translated into a single polypeptide having amino acids derived from both coding sequences. The coding sequences need not be contiguous to one another so long as the expressed sequences ultimately process to produce the desired protein.

"Identity" means, as utilized in the context of the present specification and claims, a homology comparison with respect to the degree of sameness between a first sequence and a second sequence (the first sequence may also be referred to as the "reference sequence"). Identity is expressed as the ratio N/D times 100 percent, where N is the number of identical aligned items (bases or amino acids) and D is the sum of the total number of items in the reference sequence and the total individual spaces (corresponding to items in the second sequence) introduced into the reference sequence as a result of its alignment with the second sequence. Further, the alignment by which the N/D ratio of identity is obtained is an alignment which gives essentially the largest possible percentage identity value, i.e., the largest N value (the largest number of aligned sequence items that are identical) and the smallest D value (the smallest number of individual gap spaces introduced into the reference sequence by the alignment). Ascertaining absolutely the highest possible identity value (or best alignment) is not required to report an "essentially largest identity value" since this means in the context of the present application that the percentage identity reported has a certainty deviation that limits any possible increases in the identity value due to an alternative alignment to less than one-half of a percentage point. The sequence alignment utilized to obtain the N/D percentage identity may be performed by a manual method (hand and eye alignment) or by utilizing commercially available alignment software. The parameters of the alignment software may be adjusted until an identity value is obtained which has a certainty that limits any increase in the identity value to less than one-half of a percentage point with respect to the reported identity value.

"At Least X Percent Identity" means, as used in the context of the present specification or claims, a homology comparison with respect to the degree of sameness between a first sequence and a second sequence (the first sequence may also be referred to as the "reference sequence") wherein the degree of sameness is equal to or exceeds the value "X" of the term. The "identity" value (degree of sameness) of this term is expressed as the ratio N/D times 100 percent, where N is the number of identical aligned items (bases or amino acids) and D is the sum of the total number of items in the reference sequence and the total individual spaces (corresponding to items in the second sequence) introduced into the reference sequence as a result of its alignment with the second sequence. If any alignment exists for the second sequence and the reference sequence which results in a sameness value (N/D×100%) that is equal to or greater than the value of "X" in the phrase "at least X percent identity" then the second sequence has "at least X percent identity" with respect to the reference sequence even though it may be possible to align the two sequence in a different manner such that the calculated value is less than X. The sequence alignment utilized to obtain the N/D percentage identity may be performed by a manual method (hand and eye alignment) or by utilizing commercially available alignment software, provided that the "identity" value is calculated as hereinabove described.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A DNA "coding sequence of" or a "nucleotide sequence encoding" a particular enzyme, is a DNA sequence which is transcribed and translated into a polypeptide when placed under the control of appropriate regulatory sequences.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel et al., *Nucleic Acids Res.*, 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

Unless otherwise stated, transformation was performed as described in Sambrook and Maniatis, Molecular Cloning: A Laboratory Manual, Cold Spring Harbor Laboratory, 1989.

In accordance with an aspect of the present invention, there are provided isolated nucleic acids (polynucleotides) which encode for the mature lmb polypeptide, having the deduced amino acid sequences shown in FIG. 1 (SEQ ID NO:2).

In accordance with another aspect of the present invention, there are provided isolated polynucleotides encoding the lmb polypeptides of the present invention. The deposited material is ATCC strain 12400 and by utilizing the primer sequences described herein (or their equivalent) a genomic clone comprising DNA encoding the lmb polypeptides of the present invention, in a plasmid DNA vector form maybe readily obtained (other strains or wild-type streptococcus bacteria may also be utilized to obtain the gene). As deposited with the American Type Culture Collection, 12301 Parklawn Drive, Rockville, Md. 20852, USA, the deposited strain is assigned ATCC strain Deposit No. 12400, and is available to the public.

Additionally, the nucleotide sequence of the coding regions for the *S. agalactiae* lmb gene has been submitted as an ATCC deposit of the genomic clone comprising the DNA encoding the lmb polypeptides of the present invention in a plasmid pUC19 1945. However, the DNA vector form may be readily obtained utilizing the information provided herein (other strains or wild-type streptococcus bacteria may also be utilized to obtain the gene). As deposited on Mar. 30, 1998 with the American Type Culture Collection, 12301 Parklawn Drive, Rockville, Md. 20852, USA, the deposited plasmid is assigned ATCC Deposit No. 209732, and will be made available to the public without restriction upon the issuance of a patent based upon this application.

DETAILED DESCRIPTION OF THE INVENTION

Group B Streptococci infections are a leading cause of neonatal sepsis and meningitis. The adherence of bacterial cell-surface extracellular matrix proteins is assumed to be important in the pathogenesis of infection but the genetic determinants of this process are largely unknown. According to the present invention Lmb streptococcal adhesion mediator polypeptides that are involved in such pathogenesis of a the bacterial cells, and the gene encoding such polypepties were identified and sequenced.

The polynucleotide sequence of the gene codes for a putative lipoprotein with significant homology to the streptococcal LraI adhesin family. Mutants of this locus that were created by targeted mutagenesis, demonstrated substantially diminished adherence to immobilized human laminin. The nucleotide sequence of the gene that was subsequently designated lmb (laminin binding) is present in all of the common serotypes of S. agalacriae.

To investigate the role of Lmb in the adhesion of S. agalacriae wildtype strains to human laminin, a recombinant Lmb protein harboring six consecutive histidin residues at the C-terminus was cloned and expressed in Escherichia coli. Pre-incubation of immobilized laminin with recombinant Lmb significantly reduced adherence of a streptococcal wildtype strain (090R) to laminin, whereas the diminished adherence of isogenic lmb mutants was slightly increased under the same conditions. Results suggest that Lmb mediates the attachment of S. agalacriae to laminin which may be an important factor in the pathogenesis of invasive group B streptococcal disease.

The polynucleotide of this invention according to SEQ ID NO:1 coding for the Lmb streptococcal adhesion mediator polypeptides was originally recovered from a genomic gene library derived from the GBS strain R268. Fragments of the chromosomal DNA from the GBS strain were amplified by PCR employing degenerate primers directed towards conserved glycin rich regions of bacterial proteins. The resulting products were purified and subcloned into a vector plasmid. Nucleotide sequences of the inserts were determined by automated DNA sequencing. Comparison of deduced amino acid sequences with know sequences in the Genbank database revealed clones that included fragments of a gene with significant homology to the streptococcal LraI adhesin family. Nucleotide sequences upstream and downstream of the initial chromosomal fragments were obtained by screening of a lambda phage genomic library obtained for the GBS R268 strain.

The DNA sequencing of the polynucleotide according to the present invention revealed an open reading frame of 921 nucleotides which has a typical ribosome binding site 5 nucleotides upstream of the "ATG" start codon. Putative prokaryotic promoter regions (-35 and -10 promoter regions) were identified 71 nucleotides upstream of the start codon based on sequence similarity. The deduced protein consists of 307 amino acid residues with a predicted molecular weight of 34.1 kDa. A second open reading frame of 2.4 kb starts 12 nucleotides downstream of the Lmb stop codon. The putative start codon is GTG, which is preceded by a typical ribosome binding site (GAA-GAA), putative promoter sequences are not set forth herein for the second open reading frame.

The polynucleotides of this invention were cloned and recovered from a genomic gene library from the GBS R268 strain. Clones were obtained as set forth above and sequenced. The activity of the expressed protein was verified.

All of the known LraI proteins are lipoproteins with the typical recognition sequence LxxC for the signal peptidase II at amino acid residue 16 or 17. The GBS homologue has a similar but slightly different sequence at this position (IAGC) with an exchange of leucine to isoleucine. LplA of *Bacillus subtilis* which has been shown to be a lipoprotein by radiolabelling with palmitate, is another example of this atypical recognition sequence in a gram-positive organism (Sutcliffe and Russel 1995).

Comparison of the deduced amino acid sequence with previously identified members of the LraI adhesin family revealed a 47% homology and 27% identity with psaA of *S. pneumoniae*. Similarities to the other LraI proteins was between 36 and 46%. In addition a homology of Lmb to mntc which is part of a manganese transport operon in Synechocystis (Bartsevich and Paktrasi 1995) was observed. Homology between this transport operon and the genetic loci of LraI genes has been noted earlier (Bartsevich and Paktrasi 1995). Jenkinson (Jenkinson 1994) proposed four common structural domains of the LraI proteins. A 20 residue hydrophobic leader sequence that is cleaved off by the signal peptidase II, two transmembrane domains termed B1 and B2 and the A region, which is assumed to be surface exposed and the solute binding region of the protein. These domains appear to be conserved in the Lmb gene product according to the present invention. Interestingly amino acid residues 156–197 corresponding to the a domain of the LraI family have a 50% homology to the human laminin B2 chain (see, FIG. 8).

The analysis of Northern blots performed with an lmb specific probe indicates that the gene according to the present invention is part of an operon. The transcript size of approximately 3.2 kb corresponds to the polycistronic structure of other members of this family (Fenno, LeBlanc et al. 1989) (Sampson, O'Connor et al. 1994) (Ganeshkumar, Hannam et al. 1991). The fimA locus of *Streptococcus parasanguis* encodes an ATP-binding membrane transport system (Fenno, Shaikh et al 1995). A manganese transporter of Synechocystis with homologies to several IraI genes has been identified (Bartsevich and Paktrasi 1995). Transport systems of gram-positive bacteria usually contain a solute-binding component that is lipid modified and associated with the outer region of the cytoplasmic membrane (Tam and Milton 1993). Recent work by Dintilhac (Dintilhac and Claverys 1997) proposes that all LraI adhesins are members of a specific transporter family for metals. Taken together these findings suggest that lmb is part of a transport operon.

The gene lmb gene according to the present invention is important for the laminin binding properties of S. agalactiae. Isogenic mutants of the lmb locus demonstrated substantially diminished adherence to immobilized laminin and the recombinant protein inhibits the attachment of the wild-type strain. The reduction of wildtype adherence by the recombinant protein is a strong indication that the lmb gene product mediates the interaction between group B streptococci and laminin. Since mutants generated by insertion duplication mutagenesis have the potential to cause polar effects on downstream genes, such effects may contribute to some extent to the observed phenomenon. However, that the effects of the recombinant protein on wildtype adherence, as well as the reduced adherence of mutants to laminin tend to show that such effects are minimal.

FimA from *S. parasanguis* and ScaB from *S. gordonii* have been shown to be important for the binding of these microorganisms to saliva coated hydroxylapatite (Fenno, LeBlanc et al. 1989) (Ganeshkumar, Hannam et al. 1991). Glycoproteins of the saliva are assumed to be the ligands for these adhesins. In analogy to these findings our results indicate that Lmb binds to laminin, a high molecular weight glycoprotein of the basement membrane. The homology of the putative a region with the human laminin B2 chain could be a molecular mimicry, leading to the attachment to other polypeptide chains of the laminin molecule. Laminin is a larger macromolecule that self-assembles in vitro to large aggregates without any particular order and has the ability to bind a variety other basement membrane compounds, such as nidogen, collagen IV and perlecan (Engel 1992).

The adherence of bacteria to laminin appears to be of significant importance for the development of invasive group B streptococcal infection. Invasion of *S. agalactiae* into the blood stream as well as the entry into CSF, which occurs in the case of meningitis, requires the passage of bacteria through basement membranes. The. interaction of bacterial surface proteins with laminin is an important mechanism in this context. For *H. influenzae* adhesion and penetration of the basement membranes, which are open to circulation in the fenestrated endothelium of the choroid plexus, is discussed as the route of entry into the CSF (Virkola, Lähteenmäki et al. 1996).

Immunogenic properties have been demonstrated for several members of the LraI adhesin family these include PsaA, EfaA and FimA (Viscount, Munroe et al. 1997) (Lowe, Lambert et al. 1995) (Berry and Paton 1996). For FimA a recent publication demonstrates protection against *S. parasanguis* endocarditis in an animal model after vaccination with recombinant FimA (Viscount, Munro et al. 1997). Current vaccine approaches for GBS favor the use of a cell surface protein linked to polysaccharide structures of the capsule. Given, the presence of lmb in all of the common serotypes, the polypeptides according to the present invention are very good candidates for a very effective group B streptococcal vaccine.

One means for isolating the nucleic acid molecules encoding the Lmb streptococcal adhesion mediator polypeptides of the present invention is to probe a gene library with a natural or artificially designed probe using art recognized procedures (see, for example: Current Protocols in Molecular Biology, Ausubel F.M. et al. (EDS.) Green Publishing Company Assoc. and John Wiley Interscience, New York, 1989, 1992). For example, portions of the polynucleotide sequence according to SEQ ID NO: 1 are useful as probes for obtaining the fill length gene from a genomic library. It is appreciated by one skilled in the art that the polynucleotides of SEQ ID NO:1, or fragments thereof (comprising at least 12 contiguous nucleotides), are particularly useful probes. Other particularly useful probes for this purpose are hybridizable fragments of the sequence of SEQ ID NO: 1 (i.e., comprising at least 12 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10×Denhardts, and 0.5 mg/mL polyriboadenylic acid. Approximately $2\times10^7$ cpm (specific activity $4-9\times10^8$ cpm/ug) of $^{32}P$ end-labeled oligonucleotide probe are then added to the solution. After 12–16 hours of incubation, the membrane is washed for 30 minutes at room temperature in 1×SET (150 mM NaCl, 20 mM Tris hydrochloride, pH 7.8, 1 mM $Na_2EDTA$) containing 0.5% SDS, followed by a 30 minute wash in fresh 1X SET at Tm less 10° C. for the oligo-nucleotide probe. The membrane is then exposed to auto-radiographic film for detection of hybridization signals.

Stringent conditions means hybridization will occur only if there is at least 90% identity, preferably at least 95% identity and most preferably at least 97% identity between the sequences. Further, it is understood that a section of a 100 bps sequence that is 95 bps in length has 95% identity with the 1090 bps sequence from which it is obtained. See J. Sambrook et al., *Molecular Cloning, A Laboratory Manual*, 2d Ed., Cold Spring Harbor Laboratory (1989) which is hereby incorporated by reference in its entirety. Also, it is understood that a fragment of a 100 bps sequence that is 95 bps in length has 95% identity with the 100 bps sequence from which it is obtained.

As used herein, a first DNA (RNA) sequence has a percent identity to another DNA (RNA) sequence if there is such percent identity between the bases of the first sequence and the bases of the another sequence, when properly aligned with each other, for example when aligned by BLASTN.

The present invention relates to polynucleotides which differ from the reference polynucleotide in a manner such that the change or changes is/are silent change(s), in that the amino acid sequence encoded by the polynucleotide remains the same. The present invention also relates to nucleotide changes which result in amino acid substitutions, additions, deletions, fusions and truncations in the polypeptide encoded by the reference polynucleotide. In a preferred aspect of the invention these polypeptides retain the same biological action as the polypeptide encoded by the reference polynucleotide.

The polynucleotides of the present invention may be in the form of RNA or DNA which DNA includes cDNA, genomic DNA, and synthetic DNA. The DNA may be double-stranded or single-stranded, and if single stranded may be the coding strand or non-coding (anti-sense) strand. The coding sequences which encodes the mature Lmb streptococcal adhesion mediator polypeptides according to the invention may be identical to the coding sequences shown in FIG. 1 (SEQ ID NO: 1) or may be a different coding sequence which coding sequence, as a result of the redundancy or degeneracy of the genetic code, encodes the same polypeptides and putative promoters as the DNA of FIG. 1 (SEQ ID NO:1).

As hereinabove indicated, the polynucleotides may have a coding sequence which is a naturally occurring allelic variant of the coding sequence shown in FIG. 1 (SEQ ID NO:1). As known in the art, an allelic variant is an alternate form of a polynucleotide sequence which may have a substitution, deletion or addition of one or more nucleotides, which does not substantially alter the function of the encoded polypeptide. Also, using directed and other evolution strategies, one may make very minor changes in DNA sequence which can result in major changes in function.

Fragments of the full length gene of the present invention may be used as hybridization probes for a cDNA or a genomic library to isolate the full length DNA and to isolate other DNAs which have a high sequence identity to the gene. Probes of this type preferably have at least 10, preferably at least 15, and even more preferably at least 30 bases and may contain, for example, at least 50 or more bases. In fact, probes of this type having at least up to 150 bases or greater may be utilized. The probe may also be used to identify a DNA clone corresponding to a full length transcript and a genomic clone or clones that contain the complete gene including regulatory and promotor regions, exons and introns. An example of a screen comprises isolating the coding region of the gene by using the known DNA sequence to synthesize an oligonucleotide probe. Labeled oligonucleotides, having a sequence complementary to that of the gene or portion of the gene sequences of the present invention are used to screen a library of genomic DNA to determine which members of the library the probe hybridizes to in a complementary sense, have an identity as described above.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other sources or to screen such sources for related sequences.

The present invention further relates to polynucleotides which hybridize to the hereinabove-described sequences if there is at least 70%, preferably at least 90%, and more preferably at least 95% identity between the sequences. (As indicated above, 70% identity would include within such definition a 70 bps fragment taken from a 100 bp polynucleotide, for example.) The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode Lmb streptococcal adhesion mediator polypeptides which either retain substantially the same biological function or activity as the Lmb polypeptide encoded by the DNA of FIG. 1 (SEQ ID NO:1). In referring to identity in the case of hybridization, as known in the art, such identity refers to complementarity of polynucleotide segments.

Alternatively, the polynucleotide may have at least 15 bases, preferably at least 30 bases, and more preferably at least 50 bases which hybridize to any part of a polynucleotide of the present invention and which has an identity thereto, as hereinabove described, and which may or may not retain activity. For example, such polynucleotides may be employed as probes for the polynucleotide of SEQ ID NO: 1, for example, for recovery of the polynucleotide or as a diagnostic probe or as a PCR primer.

Thus, the present invention is directed to polynucleotides having at least a 70% identity, preferably at least 90% identity and more preferably at least a 95% identity to a polynucleotide which encodes the polypeptides of SEQ ID NO:1, as well as fragments thereof, which fragments have at least 15 bases, preferably at least 30 bases, more preferably at least 50 bases and most preferably fragments having up to at least 150 bases or greater, which fragments are at least 90% identical, preferably at least 95% identical and most preferably at least 97% identical to any portion of a polynucleotide of the present invention.

The present invention further relates to polypeptides which have the deduced amino acid sequence of FIG. 1 (SEQ ID NO:1) as well as fragments, analogs and derivatives of such polypeptide.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptides of SEQ ID NO:2 (in particular the mature polypeptide) as well as polypeptides which have at least 70% similarity (preferably at least 70% identity) to the polypeptides of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptide with such portion of the polypeptide generally containing at least 30 amino acids and more preferably at least 50 amino acids and most preferably at least up to 150 amino acids.

As known in the art "similarity" between two polypeptides is determined by comparing the amino acid sequence and its conserved amino acid substitutes of one polypeptide to the sequence of a second polypeptide. The definition of 70% similarity would include a 70 amino acid sequence fragment of a 100 amino acid sequence, for example, or a 70 amino acid sequence obtained by sequentially or randomly deleting 30 amino acids from the 100 amino acid sequence.

A variant, i.e. a "fragment", "analog" or "derivative" polypeptide, and reference polypeptide may differ in amino acid sequence by one or more substitutions, additions, deletions, fusions and truncations, which may be present in any combination.

Among preferred variants of polypeptides according to the invention are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Most highly preferred are variants which retain the same biological function and activity as the reference polypeptide from which it varies.

Fragments or portions of the Lmb streptococcal adhesion mediator polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

To form such a vaccine or therapeutic agent, the polypeptide according to the present invention or a transformed vector that will generate the polypeptide according to the invention in vivo is administered in conjunction with a suitable pharmaceutical carrier. As representative examples of suitable carriers there may be mentioned: mineral oil, alum, synthetic polymers, etc. Vehicles for vaccines and therapeutic agents are well known in the art and the selection of a suitable vehicle is deemed to be within the scope of those skilled in the art from the teachings contained herein. The selection of a suitable vehicle is also dependent upon the manner in which the vaccine or therapeutic agent is to be administered. The vaccine or therapeutic agent may be in the form of an injectable dose and may be administered intramuscularly, intravenously, orally, intradermally, or by subcutaneous administration.

Other means for administering the vaccine or therapeutic agent should be apparent to those skilled in the art from the teachings herein; accordingly, the scope of the invention is not to be limited to a particular delivery form.

When the transformed host cells that express the polypeptide according to the invention are employed as a vaccine, such a vaccine can have important advantages over simply administering the polypeptide. Certain host cells have adjuvant properties and stimulate a recipient's immune system to respond with great effectiveness. A vaccine with such an aspect can induce cell-mediated immunity and thus may provide immunity against pathogens in cases where cell-mediated immunity appears to be critical for resistance. Further, certain host cells may stimulate long-term memory or immunity. Utilizing such a vaccine it thus may be possible to prime long-lasting T cell memory, which stimulates secondary antibody responses neutralizing to the streptococcal adhesion polypeptides and thus avoid streptococcal infections. Further, fragments may be utilized can be utilized from the lmb polypeptide in such a vaccine, which fragments correspond to one or more antigenic sites of the polypeptide. Such can provide pinpoint immunity that can avoid undesired cross-immunity or potential auto-immunity.

In accordance with an embodiment of the present invention, the vaccine includes the lmb polypeptide according to the invention (preferably the polypeptide having an amino acid sequence according to SEQ ID NO:2) or fragment thereof alone or in combination with other antigens (or fragments thereof), as hereinabove described. Although the polypeptide may be recovered from a soluble fraction recovered by treating the streptococcal bacteria with a detergent and/or chaotropic agent, without lysing or rupturing the organism, and then isolated with antibody specific for the polypeptide, major portion of the polypeptide may not be solubilized and may remain attached to the streptococcal cells (in particular the membrane of the cells). Alternatively, a recombinant polypeptide or fragment may be utilized, further the polypeptide may be obtained from wild strains or genetically engineered strains by procedures known in the art; for example by disrupting the cells and the use of electrophoresis or antibody recovery methods, prior to or subsequent to extracting the soluble polypeptide fraction from the cells.

Similarly, it is possible within the spirit and scope of the present invention to employ a fragment of one or more of the hereinabove described polypeptides in producing a vaccine of the present invention in place of or in conjunction with one or more of such antigens. The term fragment of the antigen as used herein is a fragment of the antigen which (1) includes an epitope which will produce an antibody which recognizes such antigen and (2) will immunoreact with the polypeptide according to the present invention The fragment will have a molecular weight lower than the molecular weight of the polypeptide described.

Thus, in accordance with an aspect of the present invention, there is provided a protein or proteins which are essentially free of streptococcal cells which protein or proteins produce an antibody or antibodies which recognizes at least one streptococcal adhesion polypeptide antigens having a molecular weight from about 10 kda to about 90 kda and preferably such antigen which is recognized has a molecular weight of at least 20 kda and most generally the molecular weight, does not exceed 75 kda. In a particularly preferred embodiment such protein or proteins produce an antibody which recognizes only the Group B Streptococcal adhesion proteins. As hereinabove indicated, in general, such protein or proteins will immunoreact with a monoclonal antibody that is specific to Group B Streptococcal adhesion polypeptides. Such protein may be the corresponding GBS adhesion polypeptide antigen and/or a fragment and/or derivative thereof. Such protein or proteins, as hereinafter indicated, may be used in combination with a physiologically acceptable vehicle as a vaccine for protecting humans or animals against GBS infections.

The GBS adhesion polypeptide antigen and/or fragment in conjunction with a physiologically acceptable carrier is employed as a vaccine to provide protection against GBS infections. Such polypeptide antigen(s) and/or fragment(s) thereof are employed in the vaccine in an amount effective to provide protection against GBS infections. In general, each dose of the vaccine contains at least 5 micrograms and preferably at least 100 micrograms of such antigen(s) and/or fragments of the antigen. In most cases the vaccine does not include such antigen(s) and/or fragment; in an amount greater than 20 milligrams.

The term "protection" or "protecting" when used with respect to the vaccine for GBS infections described herein means that the vaccine prevents GBS infections and/or reduces the severity of such infections in a host, such as a human.

If multiple doses are given, in general they would not exceed 3 doses over a six week period.

The carrier which is employed in conjunction with the GBS adhesion polypeptide antigen may be any one of a wide variety of carriers. As representative examples of suitable carriers, there may be mentioned: mineral oil, alum, synthetic polymers, etc. Carriers for vaccines are well known in the art and the selection of a suitable carrier is deemed to be within the scope of those skilled in the art from the teachings herein. The selection of a suitable carrier is also dependent upon the manner in which the vaccine is to be administered. The vaccine may be in the form of an injectable dose and may be administered intramuscularly, intravenously, or by sub-cutaneous administration. It is also possible to administer the vaccine orally by mixing the active components with food or water; providing a tablet form, etc.

Other means for administering the vaccine should be apparent to those skilled in the art from the teachings herein; accordingly, the scope of the invention is not limited to a particular delivery form.

It is also to be understood that the vaccine may include active components or adjuvants in addition to the antigen(s) or fragments thereof hereinabove described.

In accordance with a further aspect of the present invention, there is provided an assay for detection or determination of antibody to the GBS adhesion polypeptide antigen which employs a GBS adhesion polypeptide antigen, of the type hereinabove described, as a specific binder in the assay.

More particularly, there is provided an immunoassay for the GBS adhesion polypeptide antibody in which a GBS adhesion polypeptide antigen is employed as a binder, in the assay, for specifically binding the GBS adhesion polypeptide antibody.

The assay technique which is employed is preferably a sandwich type of assay wherein the GBS adhesion polypeptide antigen is supported on a solid support, as a binder, to bind GBS adhesion polypeptide specific antibody present in a sample, with the bound antibody then being determined by use of an appropriate tracer.

The tracer is comprised of a ligand. labeled with a detectable label. The ligand is one which is immunologically bound by the G13S adhesion polypeptide antibody and such ligand may be labeled by techniques known in the art.

Thus, for example, the GBS adhesion antibody bound to the GBS adhesion antigen on the solid support may be determined by the use of an antibody for the GBS adhesion antibody which is labeled with an appropriate detectable label.

In such a sandwich assay technique, the labeled antibody to the GBS adhesion antibody may be a monoclonal antibody or a polyclonal antibody; e.g. the polyclonal antibody may be anti-human IgG or may be an antibody which is specific for the GBS adhesion antibody, which antibody may be produced by procedures known in the art; for example inoculating an appropriate animal with GBS adhesion antibody.

The detectable label may be any one of a wide variety of detectable labels, including, enzymes, radioactive labels, chromogens (including both fluorescent and/or absorbing dyes) and the like. The selection of a detectable label is deemed to be within scope of those skilled in the art from teachings herein.

The solid support for the antigen may be any one of a wide variety of solid supports and the selection of a suitable support is deemed to be within the scope of those skilled in the art from the teachings herein. For example, the solid support may be a microtiter plate; a tube, a particle, etc., however, the scope of the invention is not limited to any representative support. The antigen may be supported on the support by techniques known in the art; e.g., by coating; covalent coupling, etc. The selection of a suitable technique is deemed to be within the scope of those skilled in the art from the teachings herein.

The sandwich assay may be accomplished by various techniques; e.g., "forward"; "reverse"; or "simultaneous"; however, the forward technique is preferred.

In a typical procedure, the GBS adhesion antigen, which is supported on a solid support is initially contacted with a sample containing or suspected of containing GBS adhesion antibody to specifically bind any of such antibody present in the sample to such antigen on the support.

After washing of the solid support, the support is contacted with a tracer which binds to GBS adhesion antibody. If such antibody was present in the sample, the tracer becomes bound to such antibody bound to such antigen on the solid support, and the presence of tracer on the solid support is indicative of the presence of GBS adhesion antibody in the sample. The presence of tracer may be determined by determining the presence of the detectable label by procedures known in the art.

Although the preferred procedure is a sandwich assay it is to be understood that the GBS adhesion antigen(s) may be used in other assay techniques, e.g., an agglutination assay wherein the antigen is used on a solid particle such as a latex particle.

In accordance with another aspect of the present invention, there is provided an assay or reagent kit for determining GBS adhesion antibody which includes GBS adhesion antigen, as hereinabove described, and a tracer comprised of a ligand and a detectable label. The ligand of the tracer is bound by GBS adhesion antibody. The reagents may be included in a suitable kit or reagent package. and may further include other components, such as buffers etc. The GBS adhesion antigen is preferably supported on a solid support.

Further, antibodies (such as monoclonal antibodies) that are produced as described above which are specific to the GBS adhesion polypeptide or a portion thereof may be utilized in an assay as generally described above to diagnose the presence of GBS infections in a host. Accordingly an assay diagnostic kit containing such an antibody specific for the lmb polypeptide (or for a portion of the polypeptide) is also contemplated. The other kit components and amounts for such a diagnosis are well within the skill of the ordinary practitioner to determine.

Moreover, antibodies (or an active fragment) to the polypeptide according to the invention may be used in a pharmaceutical composition to prevent or treat a streptococcal infection. Such may be admininistered in any acceptable manner in an amount effective to prevent or treat such infections. By attaching to the streptococcal adhesion polypeptide according to the invention such antibodies can deactivate the adhesion polypeptide and avoid the initial attachement of a cell to laminin. Thus, such antibodies are useful in the prevention or treatment of streptococcal infections.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector such as an expression vector. The vector may be, for example, in the form of a plasmid, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing the polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Bacillus subtilis; fungal cells, such as yeast; insect cells such as Drosophila S2 and Spodoptera Sf9; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II KS, ptrc99a, pKK223-3, pDR540, pRIT2T (Pharmacia); Eukaryotic: pXT1, pSG5 (Stratagene) pSVK3, pBPV, pMSG, pSVL SV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., *Basic Methods in Molecular Biology*, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual, Second Edition*, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis. USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

For preparation of monoclonal antibodies, any technique which provides antibodies produced by continuous cell line cultures can be used. Examples include the hybridoma technique (Kohler and Milstein, Nature, 256:495–497, 1975), the trioma technique, the human B-cell hybridoma technique (Kozbor et al., Immunology Today 4:72, 1983), and the EBV-hybridoma technique to produce human monoclonal antibodies (Cole et al., in Monoclonal Antibodies and Cancer Therapy, Alan R. Liss, Inc., pp. 77–96, 1985).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic polypeptide products of this invention.

Antibodies generated against a transcriptional promoter of the present invention may be used in screening for similar transcriptional promoters from other organisms and samples. Such screening techniques are known in the art, for example, one such screening assay is described in Sambrook and Maniatis, Molecular Cloning: A Laboratory Manual (2d Ed.), vol. 2: Section 8.49, Cold Spring Harbor Laboratory, 1989, which is hereby incorporated by reference in its entirety.

PCR Amplification of the Lmb Gene and the 2nd Open Reading Frame

A full length copy of Lmb and the second open reading frame can be generated by PCR from 500 ng–1 μg of chromosomal DNA prepared from the ATCC strain 12400 according to the method of Martin (Martin, N J, Kaplan, E L, Gerber, M A, Menegus, M A, Randolph, M, Bell, K, Cleary, P P (1990) Comparison of epidemic and endemic group G streptococci by restriction enzyme analysis. J Clin Microbiol 28: 1881–1886). The following primers can be used at a final concentration of 1 μM: N-terminal primer 5'-AGATGGTAGTTGTCATTGAC-3' (SEQ ID NO:3); C-terminal primer 5'-AGGGTTTATTTGTTGAAGTGTC-3' (SEQ ID NO:4). Nucleotides are added to a final concentration of 200 μM in 50 μM KC1, 10 μM Tris-HCl, pH 8.3, 1–2.5mM MgCl$_2$, 0.001% gelantine in a total volume of 100 μl. The PCR can be performed under the following conditions: 94° C. 5 min 30 cycles of 94° C. 1 min 53° C. 1 min 72° C. 3.5 min Typically 0.5μl of Taq-Polymerase (25U) are added after the first 5 min at 94° C.

Generation and Screen of a Lambda Genomic Library

The nucleotide sequence of the genes can be obtained from a genomic lambda library of ATCC strain 12400. Chromosomal DNA of strain ATCC 12400 can be prepared according to the method of Martin (see, citation above). For preparation of a Lambda ZAP library (Stratagene) 200 μg chromosomal DNA have to be digested with 0.2U of the Sau3A (Boehringer) restriction enzyme in a total reaction volume of 200 μl for 10–30 min at 37° C. The resulting fragments are separated according to size by a salt gradient technique (Fink, PS (1991) Using sodium chloride stepgradients to fractionate DNA fragments. BioTechniques 10: 447–449). Fractions containing 2–9 kb fragments are ligated with the BamHI-digested γ-arms and packaged using the Gigapack II packaging kit (Stratagene). Further processing and characterization of the γ-library as well as the plaque lifting onto Biodyne A membranes (Pall) can follow the manufacturer's instructions.

A 1kb probe to screen for plaques harboring the Lmb gene and the second open reading frame can be generated by PCR from strain ATCC 12400 by using 1 μg of chromosomal DNA as template and the following primers: 5'-CTACTCATATTGGAAGTTACCAG-3' (SEQ ID NO:5) and 5'-CTTCTTGGGATAATATGATAA-3' (SEQ ID NO:6). The PCR reaction conditions are as described above, amplification is carried out at: 94° C. 5 min and 30 cycles of 94° C. 1 min 53° C. 1 min 72° C. 1.5 min. The PCR products can be labeled by adding Dig-dUTP (Boehringer) at a final concentration of 5 μM to the reaction.

Hybridization with Dig-dUTP PCR products is done overnight at 65° C., the concentration of the labeled PCR product should be 5–25 μml in 6×SSC; 0.5% SDS; 5×Denhardt's solution; 100 μg/ml of denatured salm sperm DNA. Detection of positive plaques followed the manufacturer's instructions (Boehringer, Mannheim, Germany). Plaques hybridizing to the PCR probe are further analyzed by PCR. Template for PCR sequencing can be prepared by suspending the recombinant γ-phages in extraction buffer, boiling for 5 min, sedimenting the debris by centrifugation and using 5 μ of the supernatant. The inserted chromosomal fragments are amplified by using standard $T_3$ and $T_7$ primers (Stratagene) ($T_3$: 5'-AATTAACCCTCACTAAAGGG-3', $T_7$. 5¹-GTAATACGACTCACTATAGGGC-3') directed to conserved γ-phage sequences adjacent to the inserted fragment. Automated sequencing of the PCR products with $T_3$ and $T_7$ primers can follow standard protocols.

The present invention will be further described with reference to the following examples; however, it is to be understood that the present invention is not limited to such examples. All parts or amounts, unless otherwise specified, are by weight.

EXAMPLE 1

General DNA Techniques

S. agalactiae isolates were cultured on Columbia agar base (Unipath, England) supplemented with 3% sheep blood, grown in Todd-Hewitt broth (THB) (Unipath, England) or THB supplemented with 0.5% yeast extract (THY) at 37° C. Mutant strains harboring chromosomally integrated pG+host vectors were maintained in medium containing 5 mg/l erythromycin at a temperature of 39° C. Growth rates of wildtype and mutant strains were determined by measuring optical density at 600 nm in THY or THY supplemented with MnCl$_2$.

Standard recombinant DNA techniques were employed for nucleic acid preparation and analysis. Polymerase according to the manufacturer's protocol (Boehringer, Mannheim, Germany) with 35 cycles of amplification steps of 1 min at 94° C., 1 min at 50–56° C. and 1–3 min at 72° C. For PCR with degenerate primers PCR conditions were 95° C. 5 min, 35 cycles of 95° C. 30 sec, 45° C. 30 sec, 72° C. 1 min with the primers: (5'-GGG GGG ATC CRT SNN SGA YRA YGG-3'; 5'-GGG GGG ATC CAR SCC SAV SCC SNN SC-3'). Genomic streptococcal DNA was isolated as described previously (Martin, Kaplan et al. 1990). Plasmid DNA was isolated and purified using Qiaprep Spin Miniprep kit (Qiagen, Hilden, Germany) according to the manufacturer's instructions. Plasmid and PCR products were sequenced on an ABI 373 automated DNA sequencer using the ABI PRISM™ Dye terminator cycle sequencing kit (Perkin Elmer, Calif., USA). Group B streptococcal strains were transformed according to the protocol of Ricci (Ricci, Manganelli et al. 1994).

Group B streptococcal strains were transformed according to the protocol of Ricci (Picci, MangiLnelli et al. 1994).

EXAMPLE 2
Protein Techniques

For the expression of recombinant protein *E. coli* strain BL 21 harboring the pet2la::lmb construct was grown to an OD of 0.4 in LB, protein expression was induced by 1 mM IPTG for 2 hours, cells were resuspended in 50 mM TrisHCl and lysed by gjhghj. Recombinant Lmb was purified from lysed *E. coli* cells by passage over a commercial Nickel affinity matrix (QiaExpress) and eluted under native conditions via pH shifts, according to the manufacturer's instructions. The eluate was subjected to 8–25% gradient SDS-Page electrophoreses on the Phast system (Pharmacia, LKB) and stained with Coomassie brilliant blue (See FIG. 6).

EXAMPLE 3
RNA Preparation and Analysis

Total RNA was prepared from GBS sums B268 and O90R. Cells were grown to an OD of 0.6 in 7M medium supplemented with 1% fetal calf serum. Streptococci were lysed under a pressure of 16000–20000 psI using a high pressure homogenizer (Avestan Inc. Ottawa Canada). The lysate was collected on ice and 1 ml of Trizol (Gibco, BRL) reagent was added immediately. Purification of the RNA followed the manufacturer's instructions. Agarose get electrophoresis and Northern blotting was performed as described previously (Podbielski, Flosdorff et al. 1995). Hybridization with Dig-dLTTP PCR products was done overnight at 50° C., followed by stringent washing steps at 68° C. to remove unspecifically bound probe. Detection by Chemiluminescence followed the manufacturer's instructions (Boehringer).

EXAMPLE 4
Phage Techniques

A lambda Zap express library of strain O90R was created as described by Podbielski et al. (Podbielski, Flosdorff et al. 1995). Briefly 200 µg of genomic DNA were digested with 0.2U of Sau3A for 30 min. at 37° C. The resulting DNA fragments were separated according to size by a salt gradient technique. Fractions containing 2 to 9kb fragments were ligated with BamH1 digested I arms and packaged using a Gigapack 11 packaging kit (Stratagene). Further processing and plaque lifting onto nylon membranes followed the manufacturer's instructions (Stratagene).

EXAMPLE 5
Transcription Analysis of the lmb Locus

A polycistronic structure has been reported for several genes of the homologous streptococcal adhesions (Fenno, LeBlanc et al. 1989) (Berry and Paton 1996) (Ganeshkumar, Hannam et al. 1991) (Kolenbrander, Andersen et al. 1994). To analyze transcript size in Group B streptococci Northern blot analysis of the lmb locus was performed with RNA isolated from strains R268 and O90R. Total RNA was isolated from late logarithmic phase cells and electrophoresed on formaldehyde gels. A dioxygenin-dUTP labeled probe was used for the detection of lmb transcripts. It demonstrated a single band indicating that lmb is also part of an operon.

EXAMPLE 6
Adherence Assay

Adherence of *S. agalactiae* O90R wildtype and lmb mutant strains (lmb-k1, lmb-k2) to immobilized laminin was tested in Terasaki wells coated with 100 µg/ml of extracellular matrix protein. Bacteria were grown to midlogarithmic phase in THB broth, labeled with FITC washed twice and resuspended to a concentration of $10^8$/ml in DPBS+0.5% Tween. $10^6$ Bacteria per well were added and incubated for 1 hour at 37° C., after the removal of non adherent bacteria by washing, fluorescence was measured by cytofluor (gain of 92). Preincubation of immobilized laminin with recombinant Lmb (100 µg/ml) was performed at 37° C. for 20 min. before the addition of bacteria.

Figure 7:
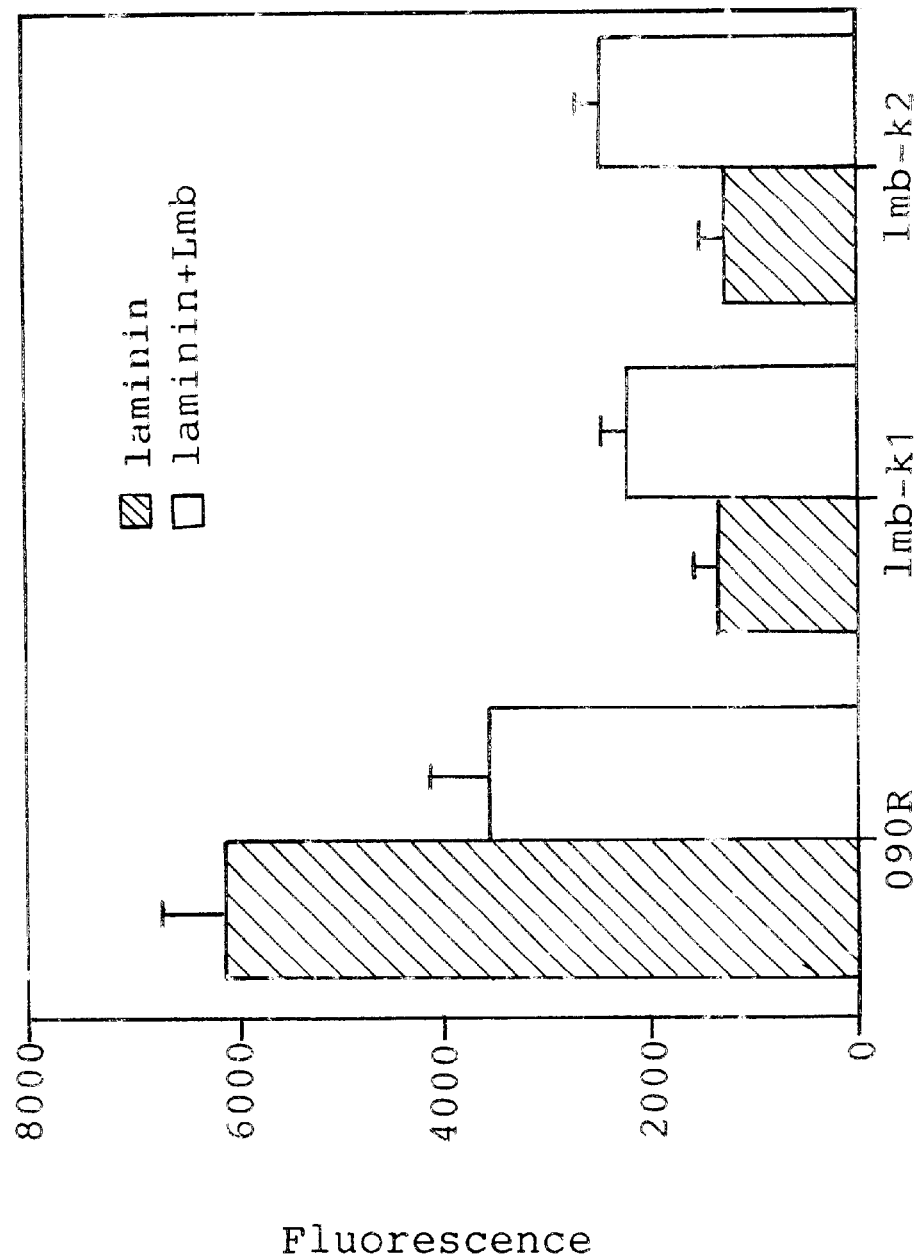
FIG. 7 illustrates the adherence of S. agalactiae 09OR wildtype and Lmb mutant strains (lmb-k1, lmb-k2) to immobilized laminin. An assay was performed utilizing Terasaki wells coated with 100 $\mu$g/ml of extracellular matrix protein. The results of the assays are shown in histogram form in the figure and the bars represent the mean +/- standard deviation for six wells. Results are averages that are representative of three independent experiments performed for each strain.

Utilizing such procedures the adherence of GBS wildtype and mutant strains to immobilized extracellular matrix proteins (ECM) was tested using fluorescence labeled bacteria and 96 well plastic dishes coated with 100 µg/ml of ECM. $10^6$ bacteria per well were allowed to adhere for 1 hour at 37° C. After the removal of non-adhering streptococci, firmly attached microorganisms were measured by fluorescence counter. In comparison to the wildtype strain O90R the adherence of two distinct lmb mutants (lmb-k1, lmb-k2) to immobilized laminin was significantly reduced. Adherence of both mutants reached only 25% of values obtained for the wildtype strain (FIG. 7). Growth characteristics of the mutants on solid media, as well as in liquid culture, were comparable to wildtype strains (data not shown), ruling out the possibility that the diminished adherence was due to impaired acquisition of nutrients.

Figure 6:
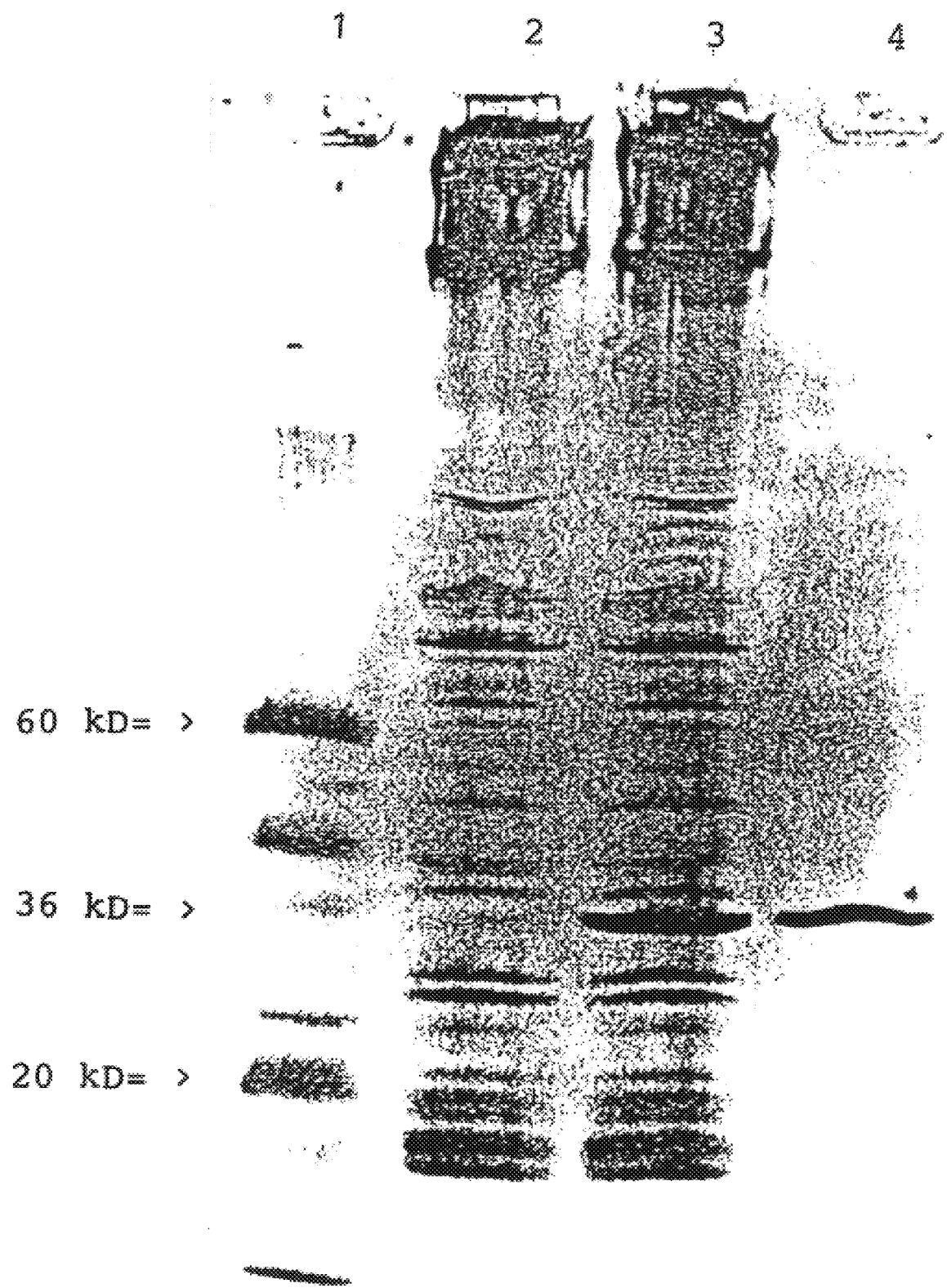
FIG. 6 illustrates the SDS-Page gel electrophoresis of recombinant Lmb. Recombinant Lmb was separated on an 8–25% SDS-Page gel along with molecular markers and stained with Coomassie brilliant blue.

EXAMPLE 7
Influence of Recombinant Protein on the Adherence of the Wildtype Strain In order to test the hypothesis that Lmb on the surface of GBS interacts with immobilized laminin a recombinant protein was generated. The lmb gene lacking the putative N-terminal signal sequence was amplified by PCR and cloned into the protein expression vector pET 21a. Recombinant Lmb protein harboring six consecutive histidin residues at the C-terminus was expressed in *E. coli* and purified under non-denaturing conditions using a nickel affinity matrix. On SDS-Page gel the recombinant protein could be visualized as a band of approximately 34 kDa, which corresponds very well to the predicted molecular weight of Lmb (FIG. 6). To evaluate the influence of Lmb on the adherence of the wildtype strain, laminin coated Terasaki plates were incubated with recombinant protein at a concentration of 100 µg/ml, prior to adherence assays. Preincubation with recombinant Lmb significantly reduced the adherence of FITC labeled bacteria. Fluorescence readings for the O90R wildtype strain were decreased to 60% of the initial values (FIG. 7). Interestingly the adherence of isogenic lmb mutants was slightly increased under the same conditions, which could be caused by association of the recombinant protein with the bacterial surface of the mutants and laminin.

EXAMPLE 8
Construction of lmb Mutants by Insertion Duplication Mutagenesis

The plasmid pG+host 5 was used for targeted genetic mutagenesis of lmb. The plasmid harbors a temperature sensitive origin of replication leading to chromosomal insertion by homologous recombination when the incubation temperature of streptococcal strains is raised to 37° C. or higher (Biswas, Gruss et al. 1993). Two mutants of the O90R wildtype strain (lmb-k1 and lmb-k2) were created by plasmid insertion at nucleotide 495 and 777 of the lmb gene respectively (FIG. 3). A third mutant (lmb-k5) was created by insertion of the vector 14 nucleosides downstream of the stop codon of lmb and 27 nucleotides upstream of the start codon of the second open reading frame. Correct chromosomal insertion of the plasmid was confirmed either by Southern blot or PCR. Chromosomal DNA of the mutant lmb-k1 and the wildtype strain O90R was digested with the restriction endonuclease EcoRI or XbaI and probed with a nucleotide probe to the duplicated fragment of lmb. The mutant strain lmb-k1 clearly showed two bands corresponding to the duplicated part of the gene (FIG. 5). PCR with primers annealing to vector sequences and genomic nucleotide sequence upstream or downstream of the duplication site was employed to confirm chromosomal insertion for lmb-k2 and lnb-k5 (data not shown).

EXAMPLE 9
Presence of lmb in Different Group B Streptococcal Serotypes

To determine the distribution of lmb in different *S. agalactiae* strains, a 430 bp fragment of the gene was amplified by PCR using the chromosomal DNA of different group B streptococcal serotypes (Ia, Ib, Ic, III-VII) as template. PCR products could be detected in all of the serotypes tested. The specificity of the products was confirmed by Southern blotting and hybridization with a 210 bp internal probe (FIG. 4).

EXAMPLE 10
Expression of Lmb in *E. coli*

The lmb gene was cloned into the pET21a expression vector (Novagen, Madison, Wis., USA) in *E. coli* strain BL21 (DE3) (Novagen, Madison, Wis., USA) for high level expression and purification over a $Ni^{2+}$ column. To construct the pET21a::lmb vector nucleotides coding for amino acid 19-306 were amplified by PCR using the following primers: 5'-GCCGCG<u>CATATG</u>TGTGATAAGTCAGCAAA CCCCA-3' and 5'-GCCGCG<u>CTCGAG</u>CTTCAACTG TTGATAGAGCACTTCC-3'. The newly introduced restriction sites NdeI and XhoI are underlined. The resulting PCR product was purified using the QiaQuick PCR purification kit (Qiagen, Hilden, Germany) according to the manufacturer's instructions. The purified product and the pET21a plasmid were digested with NdeI and XhoI, ligated and cloned into *E. coli* employing standard molecular biology techniques. For the expression of recombinant protein *E. coli* strain BL 21(DE3) (Novagen, Madison, Wis., USA) harboring the pET21a::lmb construct was grown to an OD of 0.6 at 600 nm in Luria Bertani (LB) medium, protein expression was induced by 1 mM IPTG for 2 hours, cells were pelleted and resuspended in 1 ml of lysis buffer (50mM Na-phosphate pH 8.0, 300 mM NaCl, 20 mM imidazole, 1 mg/ml lysozyme and 1mM PMSF) for 30 min on ice and subsequent sonication was performed. Recombinant Lmb was purified from lysed *E. coli* cells by passage over a commercial Nickel affinity matrix (Ni-NTA Spin kit, Qiagen, Hilden, Germany) and eluted under native conditions, according to the manufacturer's instructions. The eluate was subjected to 8–25% gradient SDS-PAGE on the Phastsystem (Pharmacia, LKB Uppsala, Sweden) and visualized by Silver strain.

EXAMPLE 11
Subcellular Localization

Polyclonal antibodies for Lmb were obtained from Eurogentec (Eurogentec, Ougrée, Belgium). Antibodies were raised in New Zealand white rabbits by intradermic injection of 100 μg of purified recombinant Lmb at days 0, 14, 28 and 56.

Subcellular fractions were prepared from group B streptococcal strain 090R. Bacteria were grown to late logarithmic phase in THB (Todd Hewitt broth) supplemented with 3% sheep blood. Cells were disrupted at a pressure of 16 000–20 000 PSI using a high pressure homogenizer (Avestin Inc., Ottawa, Canada), cytoplasmic and membrane fractions were separated by centrifugation at 100 000 g in a Beckman airfuge. Proteins of the supernatant containing the cytoplasmic contents were precipitated by trichloroacetin acid while the pellets containing the membranes were used directly. Samples of both fractions containing 6 μg of protein each were solubilized with an SDS gel electrophoresis buffer, separated by denaturing SDS-PAGE on a 8–25% gradient gel and transferred to an Immobilin P™ PVDF membrane (Millipore, Eschbom, Germany) with the Phastsystem (Pharmacia LKB) according to the manufacturer's instructions. The blots were probed with a polyclonal anti-Lmb antibody at a dilution of 1:1000. Controls were probed with rabbit serum obtained prior to immunization at a dilution of 1:1000. Primary antibodies were detected by an alkaline phosphatase labeled anti-rabbit IgG secondary antibody (Pierce, St. Augustin, Germany) at a dilution of 1:5000. Bound antibodies were visualized by chemiluminescent CSPD (Serva, Heidelberg, Germany) according to the manufacturer's instructions.

EXAMPLE 12
RNA Preparation and Analysis

Total RNA was prepared from GBS strains R268 grown to an OD of 0.8 in THB medium. Cells were lysed mechanically by glass beads in a cell disrupter (Dianova) in the presence of 1 ml of Trizol™ (Gibco BRL, Eggenstein, Germany). Purification of the RNA followed the manufacturer's instructions. The reverse transcription was carried out with 100 ng or 1 μg of RNA as template, 2 pmol of primer (5'-GCAGCAGCAGCAGGCAGCACTGATT TGATCC-3') 0.1M DTT, 10 mM dNTP Mix, 200 U of SUPERSCRIPT II reverse transcriptase (GibcoBRL) in 50 mM Tris-HCl (pH 8.3), 75 mM KCl, 3 mM $MgCl_2$ at 42° C. for 50 min a 20 μl reaction volume. 5 μl of the reaction was used as template for a subsequent PCR reaction with the following primers: (5'-ACCGTCTGTAAATGATGTGG-3' and 5'-CGTCGTCGTCGTCCT-3').

EXAMPLE 13
Phage Techniques

A lambda Zap express library of strain O90R was created as described by Podbielski et al. (Podbielski, Flosdorff et al. 1995). Briefly 200 μg of genomic DNA were digested with 0.2U of Sau3A (Boehringer, Mannheim, Germany) for 30 min. at 37° C. The resulting DNA fragments were separated according to size by a salt gradient technique (Fink 1991). Fractions containing 2 to 9 kb fragments were ligated with BamHI digested λ arms and packaged using a Gigapack II packaging kit (Stratagene GmBH, Heidelberg, Germany). Further processing and plaque lifting followed the manufacturer's instructions. The library was screened by hybridization with PCR products at 65° C. overnight. The PCR products were labeled by adding Dig-dUTP (Boehringer) at a final concentration of 5 μM to the reaction and detection of positive plaques followed the manufacturer's instructions.

EXAMPLE 14

Adherence Assay

To study adherence of S. agalactiae 090R wildtype and lmb mutant strains (lmb-k1, lmb-k2) to immobilized laminin, 60-well Terasaki plates were coated with 100 μg/ml of laminin (Gibco BRL, Eggenstein, Germany) reconstituted in Dulbecco's phosphate buffered saline (DPBS). Plates were incubated with laminin for 18 h at room temperature. Streptococci were grown in THB broth, harvested in mid-logarithmic phase and washed twice in DPBS. Bacteria were labeled with fluorescein isothiocyanate and resuspended in DPBS. To obtain single cells bacterial suspensions were sonicated. Laminin coated wells were washed with DPBS before 10 μl of DPBS containing $5 \times 10^6$ bacteria were added to each well. For the Mn supplementation studies $MnCl_2$ was added to a concentration of 10 μM to the growth medium and DPBS. To investigate the effect of recombinant Lmb on the adherence of the 090R wildtype strain, Terasaki wells were preincubated for 20 min at 37° C. with 1 μg of recombinant Lmb before the bacterial suspension was added. After incubation for 60 min at 37° C., non-adherent bacteria were removed by washing five times with DPBS. Adherent bacteria were quantified using a fluorescence counter (Cytofluor II, Perseptive Biosystems Inc., Framingham, Mass.).

Numerous modifications and variations of the present invention are possible in light of the above teachings and, therefore, within the scope of the appended claims, the invention may be practiced otherwise than as particularly described.

What is claimed is:

1. An isolated polynucleotide consisting of SEQ ID NO: 1.
2. An isolated polynucleotide consisting of nucleotides 147 to 1017 of SEQ ID NO: 1.
3. An isolated polynucleotide consisting of a polynucleotide consisting of a polynucleotide encoding amino acid residues 1 to 290 of SEQ ID NO: 2.
4. An isolated polynucleotide consisting of a polynucleotide encoding amino acid residues −16 to −290 SEQ ID NO: 2.
5. An isolated polynucleotide consisting of the full length complement of the polynucleotide of claim 1.
6. An isolated polynucleotide consisting of the full length complement of the polynucleotide of claim 2.
7. An isolated polynucleotide consisting of the full length complement of the polynucleotide of claim 3.
8. An isolated polynucleotide consisting of the full length complement of the polynucleotide of claim 4.
9. A recombinant vector including the polynucleotide of claim 1.
10. A recombinant vector including the polynucleotide of claim 2.
11. A recombinant vector including the polynucleotide of claim 3.
12. A recombinant vector including the polynucleotide of claim 4.
13. A recombinant host cell including the polynucleotide of claim 1.
14. A recombinant host cell including the polynucleotide of claim 2.
15. A recombinant host cell including the polynucleotide of claim 3.
16. A recombinant host cell including the polynucleotide of claim 4.
17. A method for producing a polypeptide comprising expressing from the recombinant host cell of claim 13 the polypeptide encoded by said polynucleotide.
18. A method for producing a polypeptide comprising expressing from the recombinant host cell of claim 14 the polypeptide encoded by said polynucleotide.
19. A method for producing a polypeptide comprising expressing from the recombinant host cell of claim 15 the polypeptide encoded by said polynucleotide.
20. A method for producing a polypeptide comprising expressing from the recombinant host cell of claim 16 the polypeptide encoded by said polynucleotide.

\* \* \* \* \*

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1020 NUCLE OTIDES
      (B) TYPE: NUCLEIC ACID
      (C) STRANDEDNESS: SIN GLE
      (D) TOPOLOGY: LINEAR (ii) MOLECULE TYPE: DNA (xi) SEQUENCE DESCRIPTION: SEQ ID NO :1:

```
TGATGTGATA AAAGATGGTA GTTTGTCATT GACAAAGCAT TGATAAAGGAG TAAAATTAAC      61

TGGTTAATAA CTGGTTAAAT TATAATTGAG GAGGTACT ATG AAA AAA  GTT TTT TTT    117
                                          Met Lys Lys Val Phe Phe
                                                  -15

CTC ATG GCT ATG GTT GTG AGT TTA GTA ATG A TA GCA GGG TGT GAT          1 62
Leu Met Ala Met Val Val Ser Leu Val Met I le Ala Gly Cys Asp
-10                 -5                  1                 5

AAG TCA GCA AAC CCC AAA CAG CCT ACG CAA G GC ATG TCA GTT GTA          2 07
Lys Ser Ala Asn Pro Lys Gln Pro Thr Gln G ly Met Ser Val Val
                10                  15                  20

ACC AGC TTT TAC CCA ATG TAT GCG ATG ACA A AA GAA GTA TCT GGA          2 52
Thr Ser Phe Tyr Pro Met Tyr Ala Met Thr L ys Glu Val Ser Gly
                25                  30                  35

GAC CTA AAT GAT GTG AGG ATG ATC CAA TCA G GT GCG GGC ATT CAT          2 97
Asp Leu Asn Asp Val Arg Met Ile Gln Ser G ly Ala Gly Ile His
                40                  45                  50

TCC TTT GAA CCG TCT GTA AAT GAT GTG GCA G CT ATT TAT GAC GCG          3 42
Ser Phe Glu Pro Ser Val Asn Asp Val Ala A la Ile Tyr Asp Ala
                55                  60                  65

GAT TTG TTT GTT TAC CAT TCA CAT ACC TTA G AA GCT TGG GCA AGG          3 87
Asp Leu Phe Val Tyr His Ser His Thr Leu G lu Ala Trp Ala Arg
                70                  75                  80

GAT CTA GAC CCT AAT TTA AAA AAA TCA AAG G TT AAC GTG TTT GAA          4 32
Asp Leu Asp Pro Asn Leu Lys Lys Ser Lys V al Asn Val Phe Glu
                85                  90                  95

GCG TCA AAA CCT CTG ACA CTA GAT AGA GTC A AA GGG CTA GAA GAT          4 77
Ala Ser Lys Pro Leu Thr Leu Asp Arg Val L ys Gly Leu Glu Asp
                100                 105                 110

ATG GAA GTC ACA CAA GGC ATT GAC CCT GCG A CA CTT TAT GAC CCA          5 22
```

```
Met Glu Val Thr Gln Gly Ile Asp Pro Ala Thr Leu Tyr Asp Pro
                115                 120                 125

CAT ACC TGG ACG GAT CCC GTT TTA GCT GGT GAG GAA GCT GTT AAT        567
His Thr Trp Thr Asp Pro Val Leu Ala Gly Glu Glu Ala Val Asn
                130                 135                 140

ATC GCT AAA GAG CTA GGA CAT TTG GAT CCT AAA CAC AAA GAC AGT        612
Ile Ala Lys Glu Leu Gly His Leu Asp Pro Lys His Lys Asp Ser
                145                 150                 155

TAC ACT AAA AAG GCT AAG GCT TTC AAA AAA GAA GCA GAG CAA CTA        657
Tyr Thr Lys Lys Ala Lys Ala Phe Lys Lys Glu Ala Glu Gln Leu
                160                 165                 170

ACT GAA GAA TAC ACT CAA AAA TTT AAA AAG GTG CGC TCA AAA ACA        702
Thr Glu Glu Tyr Thr Gln Lys Phe Lys Lys Val Arg Ser Lys Thr
                175                 180                 185

TTT GTG ACG CAA CAC ACG GCA TTT TCT TAT CTG GCT AAA CGA TTC        747
Phe Val Thr Gln His Thr Ala Phe Ser Tyr Leu Ala Lys Arg Phe
                190                 195                 200

GGC TTG AAA CAA CTT GGT ATC TCG GGT ATT TCT CCA GAG CAA GAG        792
Gly Leu Lys Gln Leu Gly Ile Ser Gly Ile Ser Pro Glu Gln Glu
                205                 210                 215

CCC TCT CCT CGC CAA TTG AAA GAA ATT CAA GAC TTT GTT AAA GAA        837
Pro Ser Pro Arg Gln Leu Lys Glu Ile Gln Asp Phe Val Lys Glu
                220                 225                 230

TAC AAC GTC AAG ACT ATT TTT GCA GAA GAC AAC GTC AAC CCC AAA        882
Tyr Asn Val Lys Thr Ile Phe Ala Glu Asp Asn Val Asn Pro Lys
                235                 240                 245

ATT GCT CAT GCT ATT GCG AAA TCA ACA GGA GCT AAA GTA AAG ACA        927
Ile Ala His Ala Ile Ala Lys Ser Thr Gly Ala Lys Val Lys Thr
                250                 255                 260

TTA AGT CCA CTT GAA GCT GCT CCA AGC GGA AAC AAG ACA TAT CTA        972
Leu Ser Pro Leu Glu Ala Ala Pro Ser Gly Asn Lys Thr Tyr Leu
                265                 270                 275

GAA AAT CTT AGA GCA AAT TTG GAA GTG CTC TAT CAA CAG TTG AAG       1017
Glu Asn Leu Arg Ala Asn Leu Glu Val Leu Tyr Gln Gln Leu Lys
                280                 285

TAA                                                                1020
```

(2) INFORMATION FOR SEQ ID NO:2:

(i) SEQUENCE CHARACTERISTICS:
        (A) LENGTH: 306 AMINO ACIDS
        (B) TYPE: AMINO ACID
        (D) TOPOLOGY: LINEAR (ii) MOLECULE TYPE: PROTEIN (xi) SEQUENCE DESCRIPTION: SEQ ID NO:2:

```
Met Lys Lys Val Phe Phe Leu Met Ala Met Val Val Ser Leu Val
    -15                 -10                 -5

Met Ile Ala Gly Cys Asp Lys Ser Ala Asn Pro Lys Gln Pro Thr
    1                   5                   10

Gln Gly Met Ser Val Val Thr Ser Phe Tyr Pro Met Tyr Ala Met
    15                  20                  25

Thr Lys Glu Val Ser Gly Asp Leu Asn Asp Val Arg Met Ile Gln
    30                  35                  40

Ser Gly Ala Gly Ile His Ser Phe Glu Pro Ser Val Asn Asp Val
    45                  50                  55

Ala Ala Ile Tyr Asp Ala Asp Leu Phe Val Tyr His Ser His Thr
    60                  65                  70
```

-continued

```
Leu Glu Ala Trp Ala Arg Asp Leu Asp Pro Asn Leu Lys Lys Ser
 75                  80                  85

Lys Val Asn Val Phe Glu Ala Ser Lys Pro Leu Thr Leu Asp Arg
 90                  95                 100

Val Lys Gly Leu Glu Asp Met Glu Val Thr Gln Gly Ile Asp Pro
105                 110                 115

Ala Thr Leu Tyr Asp Pro His Thr Trp Thr Asp Pro Val Leu Ala
120                 125                 130

Gly Glu Glu Ala Val Asn Ile Ala Lys Glu Leu Gly His Leu Asp
135                 140                 145

Pro Lys His Lys Asp Ser Tyr Thr Lys Lys Ala Lys Ala Phe Lys
150                 155                 160

Lys Glu Ala Glu Gln Leu Thr Glu Glu Tyr Thr Gln Lys Phe Lys
165                 170                 175

Lys Val Arg Ser Lys Thr Phe Val Thr Gln His Thr Ala Phe Ser
180                 185                 190

Tyr Leu Ala Lys Arg Phe Gly Leu Lys Gln Leu Gly Ile Ser Gly
195                 200                 205

Ile Ser Pro Glu Gln Glu Pro Ser Pro Arg Gln Leu Lys Glu Ile
210                 215                 220

Gln Asp Phe Val Lys Glu Tyr Asn Val Lys Thr Ile Phe Ala Glu
225                 230                 235

Asp Asn Val Asn Pro Lys Ile Ala His Ala Ile Ala Lys Ser Thr
240                 245                 250

Gly Ala Lys Val Lys Thr Leu Ser Pro Leu Glu Ala Ala Pro Ser
255                 260                 265

Gly Asn Lys Thr Tyr Leu Glu Asn Leu Arg Ala Asn Leu Glu Val
270                 275                 280

Leu Tyr Gln Gln Leu Lys
285                 290
```

(2) INFORMATION FOR SEQ ID NO:3:

(i) SEQUENCE CHARACTERISTICS:
        (A) LENGTH: 20 NUCLEOTIDES
        (B) TYPE: NUCLEIC ACID
        (C) STRANDEDNESS: SINGLE
        (D) TOPOLOGY: LINEAR (ii) MOLECULE TYPE: DNA (xi) SEQUENCE DESCRIPTION: SEQ ID NO:3:

AGATGGTAGT TGTCATTGAC                                           20

(2) INFORMATION FOR SEQ ID NO:4:

(i) SEQUENCE CHARACTERISTICS:
        (A) LENGTH: 22 NUCLEOTIDES
        (B) TYPE: NUCLEIC ACID
        (C) STRANDEDNESS: SINGLE
        (D) TOPOLOGY: LINEAR (ii) MOLECULE TYPE: DNA (xi) SEQUENCE DESCRIPTION: SEQ ID NO:4:

AGGGTTTATT TGTTGAAGTG TC                                        22

(2) INFORMATION FOR SEQ ID NO:5:

(i) SEQUENCE CHARACTERISTICS:

```
        (A) LENGTH:  23 NUC LEOTIDES
        (B) TYPE:  NUCLEIC ACID
        (C) STRANDEDNESS:  SIN GLE
        (D) TOPOLOGY:  LINEAR (ii) MOLECULE TYPE:  DNA (xi) SEQUENCE DESCRIPTION:  SEQ ID NO :5:

CTACTCATAT TGGAAGTTAC CAG                                              23

(2) INFORMATION FOR SEQ ID NO:6:

(i) SEQUENCE CHARACTERISTICS:
        (A) LENGTH:  21 NUC LEOTIDES
        (B) TYPE:  NUCLEIC ACID
        (C) STRANDEDNESS:  SIN GLE
        (D) TOPOLOGY:  LINEAR (ii) MOLECULE TYPE:  DNA (xi) SEQUENCE DESCRIPTION:  SEQ ID NO :6:

CTTCTTGGGA TAATATGATA A                                                21
```